United States Patent
Brizzi et al.

(10) Patent No.: US 10,716,813 B2
(45) Date of Patent: Jul. 21, 2020

(54) PHARMACEUTICAL CARRIERS CONTAINING MIRNAS FOR USE IN THE TREATMENT OF FIBROTIC DISEASES CAUSED BY HYPERGLYCEMIA

(71) Applicant: UNICYTE EV AG, Oberdorf (CH)

(72) Inventors: Maria Felice Brizzi, Turin (IT); Giovanni Camussi, Turin (IT)

(73) Assignee: UNICYTE EV AG, Oberdorf (CH)

( * ) Notice: Subject to any disclaimer, the term of this patent is extended or adjusted under 35 U.S.C. 154(b) by 0 days.

(21) Appl. No.: 16/099,353

(22) PCT Filed: May 4, 2017

(86) PCT No.: PCT/EP2017/060612
§ 371 (c)(1),
(2) Date: Nov. 6, 2018

(87) PCT Pub. No.: WO2017/191234
PCT Pub. Date: Nov. 9, 2017

(65) Prior Publication Data
US 2019/0209619 A1    Jul. 11, 2019

(30) Foreign Application Priority Data

May 6, 2016 (EP) ..................................... 16168546

(51) Int. Cl.
| | | |
|---|---|---|
| C07H 21/02 | (2006.01) |
| C07H 21/04 | (2006.01) |
| A61K 35/28 | (2015.01) |
| A61K 35/407 | (2015.01) |
| A61K 48/00 | (2006.01) |
| A61P 3/10 | (2006.01) |
| A61K 9/127 | (2006.01) |
| A61K 31/7105 | (2006.01) |

(52) U.S. Cl.
CPC .............. *A61K 35/28* (2013.01); *A61K 9/127* (2013.01); *A61K 31/7105* (2013.01); *A61K 35/407* (2013.01); *A61K 48/00* (2013.01); *A61P 3/10* (2018.01)

(58) Field of Classification Search
CPC ......................... C12N 2310/11; C12N 15/113
See application file for complete search history.

(56) References Cited

FOREIGN PATENT DOCUMENTS

| EP | 2010663 | 3/2015 | |
|---|---|---|---|
| WO | WO 2006/126219 | 11/2006 | |
| WO | WO 2010/151640 | 12/2010 | |
| WO | WO 2011/057003 A2 * | 5/2011 | ........... C12N 15/113 |
| WO | WO 2011/143499 | 11/2011 | |
| WO | WO 2012/020307 | 2/2012 | |
| WO | WO 2014/013258 | 1/2014 | |
| WO | WO 2015/052526 | 4/2015 | |

OTHER PUBLICATIONS

Liu et al. (Cell Metab. Apr. 2015, 21(4), 584-595).*
Chen et al. (Methods Molecular Biol, 2013, vol. 1024.pp. 69-86, Chapter 6).*
Qian et al. (Endocrinology, 2009, 150(10), 4734-4743).*
Grundmann et al. (Circulation, Mar. 8, 2011;123(9):999-1009).*
Hwang et al. ( BMB Rep. 2011; 44(8): 506-511).*
Ohno et al. (Int J Mol Sci. Feb. 6, 2016;17(2):172).*
Ban et al. Fibrosis in diabetes complications: Pathogenic mechanisms and circulating and urinary marker. Vascular Health and Risk Management 2008:4(3), pp. 575-596.
Yang, An overview of viral and nonviral delivery systems for microRNA. Int J Pharm Investig. Oct.-Dec. 2015: 5(4): 179-181.
Deregibus et al. Endothelial progenitor cell-derived microvesicles activate an angiogenic program in endothelial cells by a horizontaltransfer of mRNA. Blood, Oct. 1 , 2007, vol. 110, No. 7, pp. 2440-2448.
Olgasi et al. DNA vaccination against rnbKitL: A new approach to inhibiting tumor growth and angiogenesis. Eur J. Cancer. 50, 234-246 (2014).
Lee et al. MicroRNA genes are transcribed by RNA polymerage II., The EMBO Journal. vol. 23, No. 20, 2004, pp. 4051-4060.
Yuan et al. Transfer of microRNA by embryonic stem cell microvescies. PloS One, vol. 4, Issue 3, Mar. 2009, e4722.
Togliatto et al. Unacylated ghrelin rescues endothelial progenitor cell function in individuals with type 2 diabetes. Diabetes. 59, 1016-1025 (2010).
Fuhrmann et al. Active loading into extracellular vesicles significantly improves the cellular uptake and photodynamic effect of porphyrins. Journal of Controlled Release. 205 (2015), pp. 35-44.
Rani et al. Mesenchymal stem cell-derived extracellular vesicles: Toward cell-free therapeutic applications. Molecular Therapy, vol. 23, No. 5, Mar. 19, 2015, pp. 812-823.
McClelland et al. MiR-21 promotes renal fibrosis in diabetic nephropathy by targeting PTEN and SMAD 7, Clinical Science, vo. 129, No. 12, Nov. 11, 2015, pp. 1237-1249.
Gallo et al. Stem cell-derived, microRNA-carrying extracellular vesicles: A novel approach to interfereing with mesangial cell collagen production in a hyperglycaemic setting. PLOS One, vol. 11, No. 9, Sep. 9, 2016, p. E0162417.
Wang et al. Influence of erythropoietin on microvesicles derived from mesenchymal stem cells protecting renal function of chronic kidney disease. Stern Cell Research and Therapy. vol. 45, No. 1, Dec. 22, 2015, pp. 256.
He et al. Bone marrow stem cells-derived microvesicles protect against enal injury in the mouse remnant kidney model. Nephrology, vol. 17, No. 5, Jul. 24, 2012, pp. 493-500.

(Continued)

*Primary Examiner* — Amy H Bowman
(74) *Attorney, Agent, or Firm* — Jacobson Holman, PLLC.

(57) ABSTRACT

The invention relates to a new therapeutic application of pharmaceutically acceptable carriers containing miR222. In particular, the invention relates to the use of extracellular vesicles (EVs) which contain the microRNA miR222, in the treatment of fibrotic disease caused by hyperglycaemia, such as diabetic nephropathy and/or renal fibrosis.

4 Claims, 7 Drawing Sheets

(56) References Cited

OTHER PUBLICATIONS

Collino et al. Microvesicles derived from adult human bone marrow and tissue specific mesenchymal stem cells shuttle selected pattern of miRNAs. PLOS One, vol. 5, No. 7, Jul. 27, 2010, p. e11803.
Jansen et al. Endothelial microparticles reduce ICAM-1 expression in a microRNA-222-dependent mechanism, Journal of Cellular and Molecular Medicine, Jun. 1, 2015.

* cited by examiner

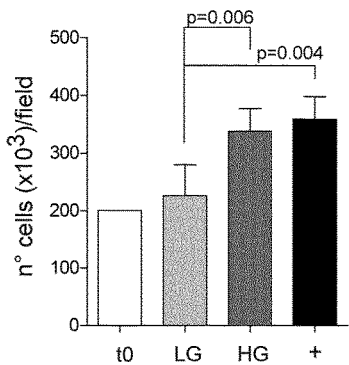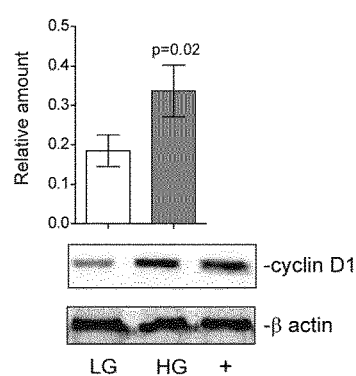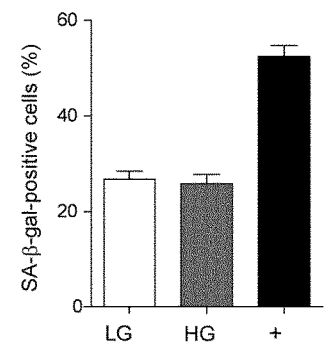
FIG.1A  FIG.1B  FIG.1C
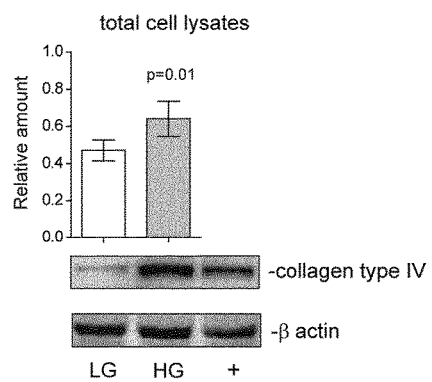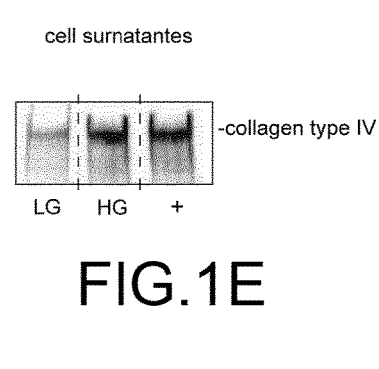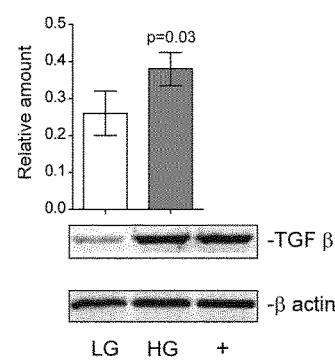
FIG.1D  FIG.1E  FIG.1F
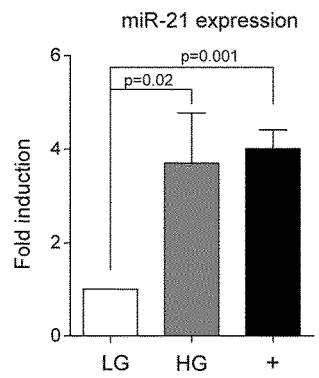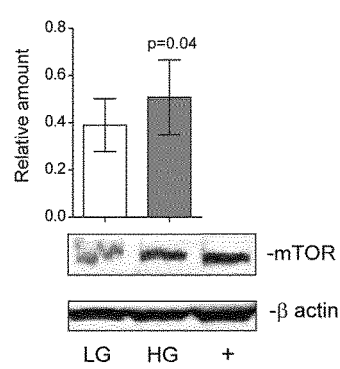
FIG.1G  FIG.1H

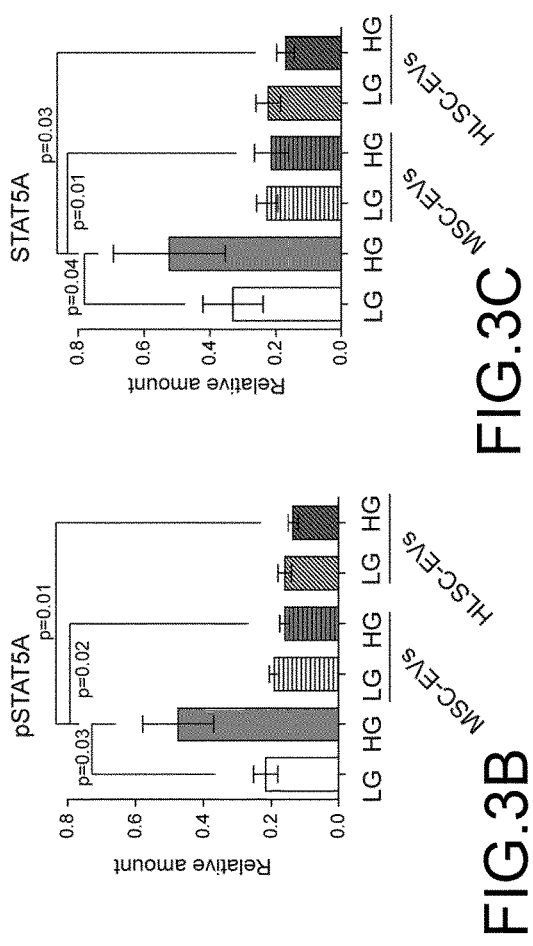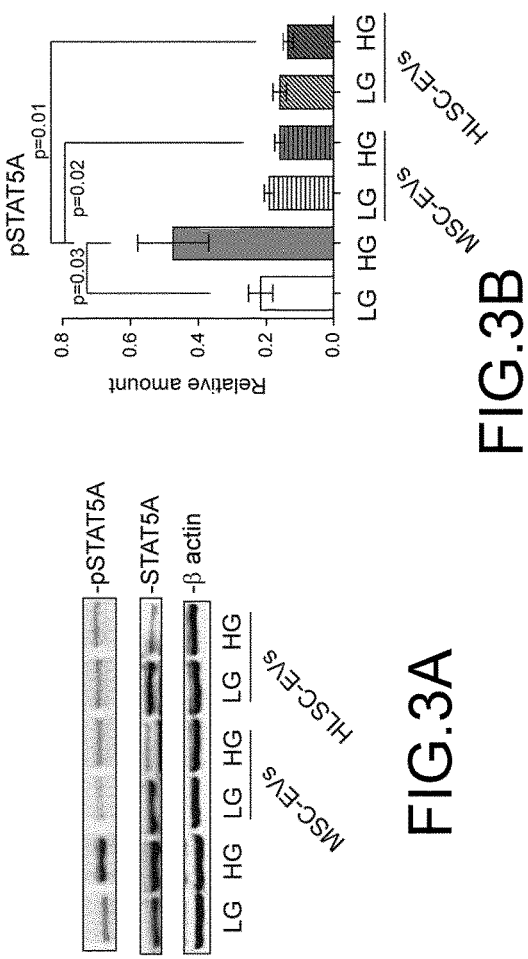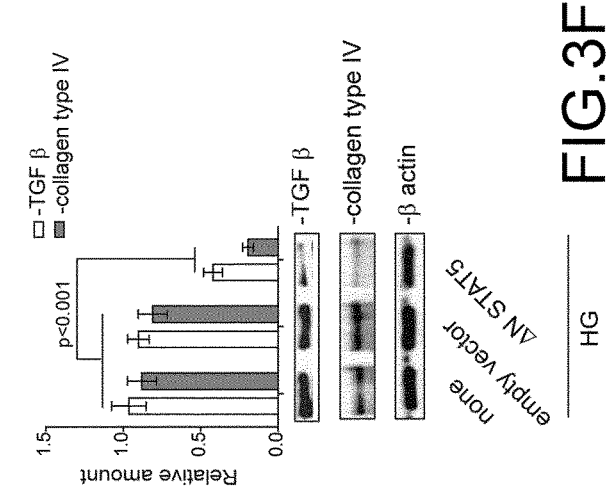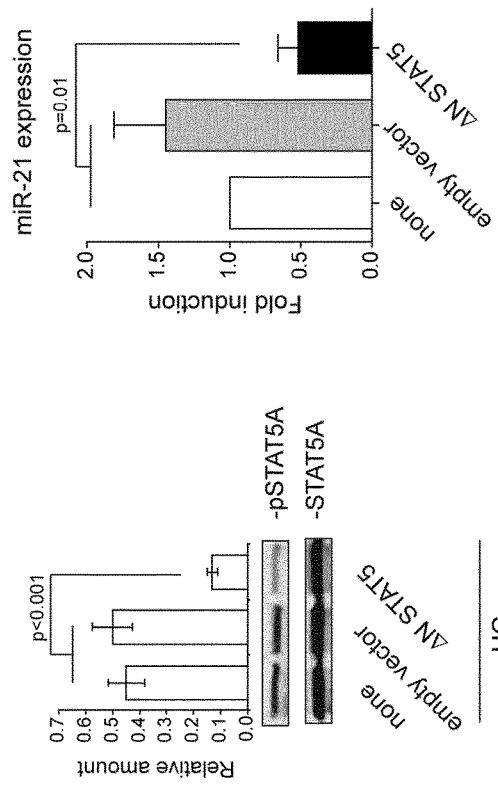

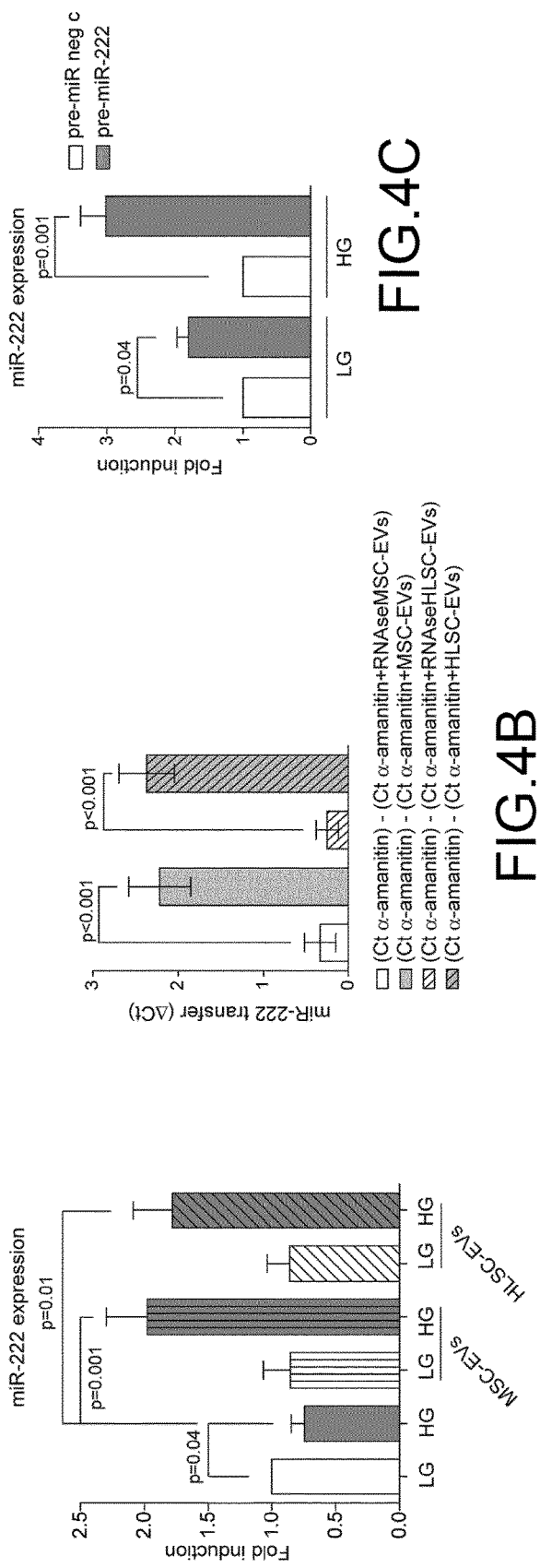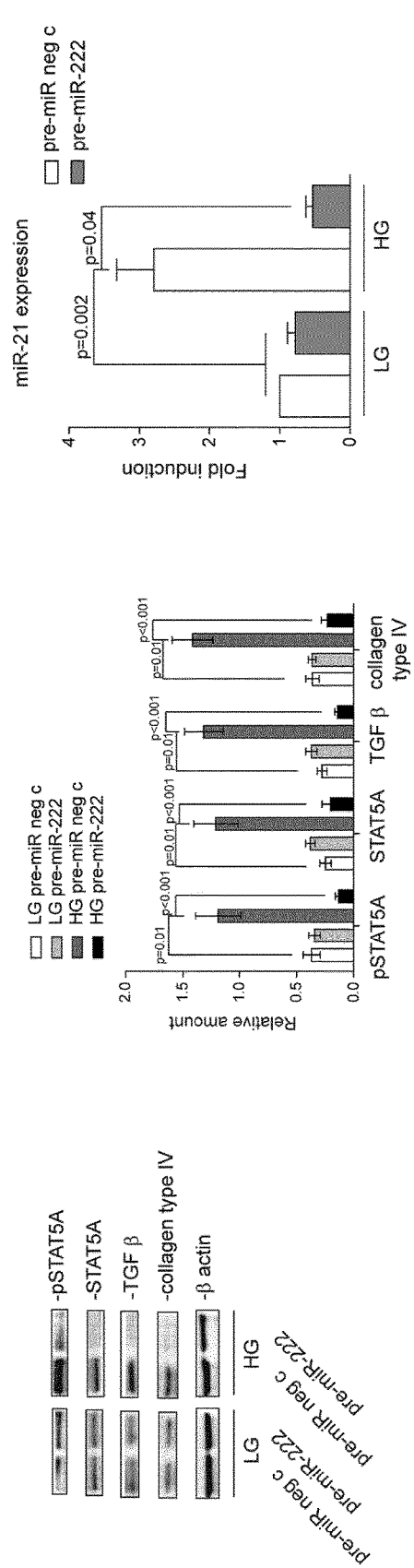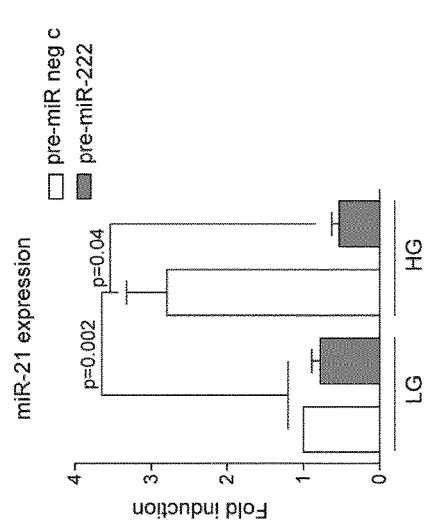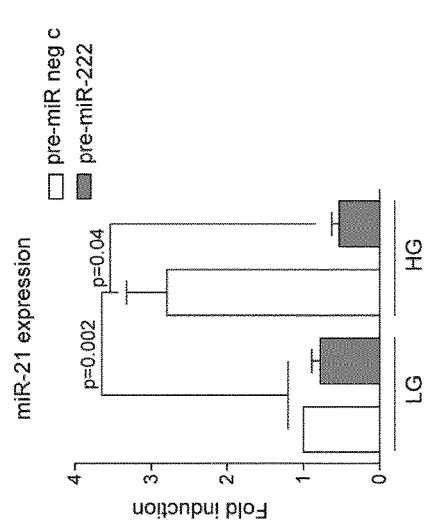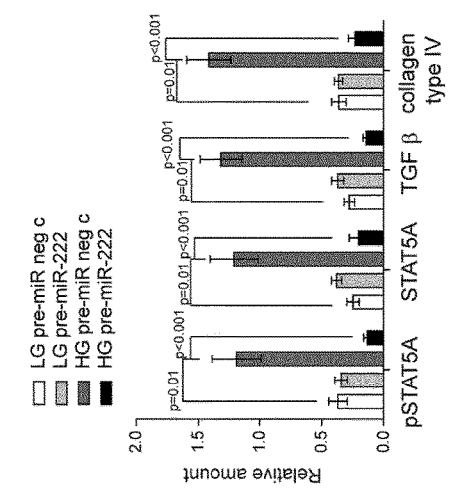

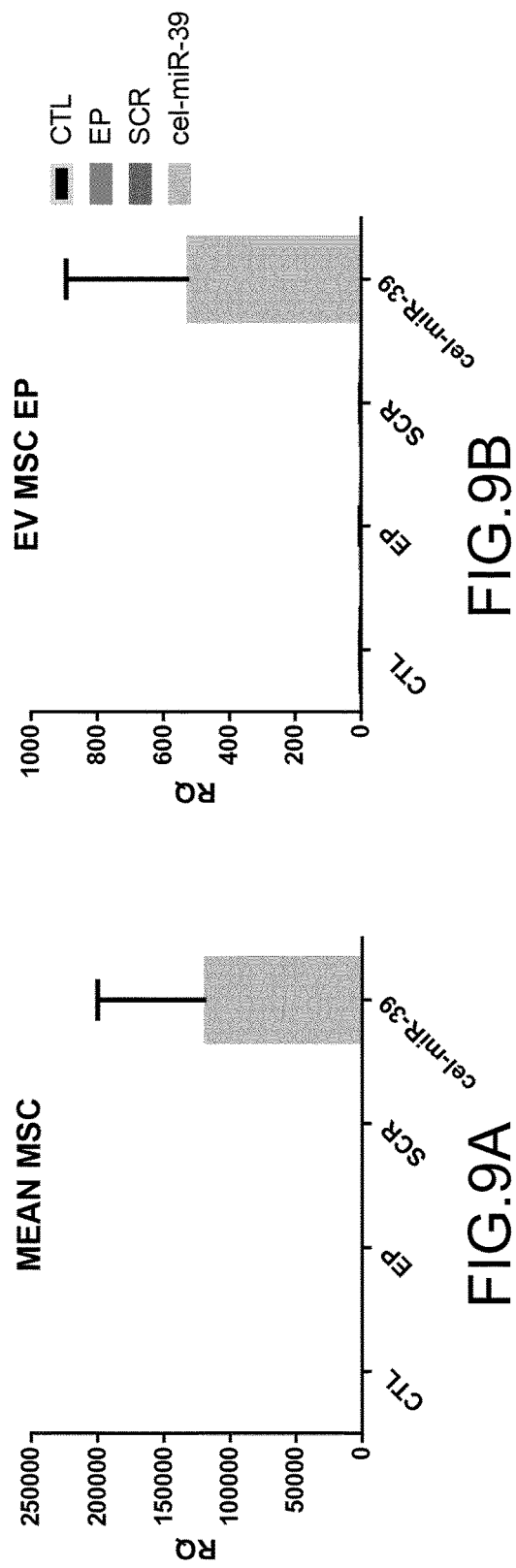
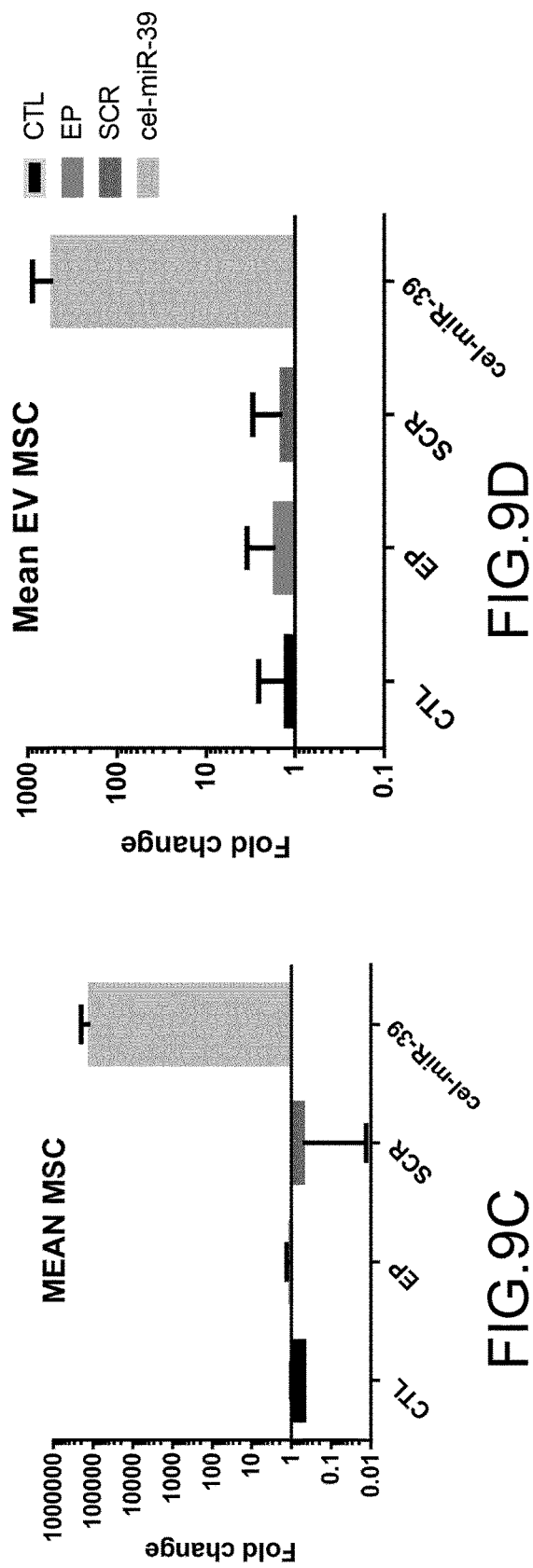

PHARMACEUTICAL CARRIERS CONTAINING MIRNAS FOR USE IN THE TREATMENT OF FIBROTIC DISEASES CAUSED BY HYPERGLYCEMIA

The present invention relates to a new therapeutic treatment of fibrotic diseases. More in in particular, the present invention relates to the use of pharmaceutical carriers, such as extracellular vesicles (EVs) derived from stem cells, in the treatment of fibrotic diseases caused by hyperglycemia. A focus lies on fibrotic renal diseases such as diabetic nephropathy.

Fibrosis is often observed following tissue injury. Fibrosis induced by hyperglycemia is a special type of fibrosis found in diabetic patients. The kidney is often affected by such fibrotic diseases.

Diabetes is the main driver of chronic kidney disease (CKD) in the Western world, accounting for about 50% of new cases. Almost 40% of diabetes sufferers develop diabetic nephropathy (DN), which has thus become the leading cause of end stage renal disease (ESRD) in urbanized countries. Patients with CKD are at increased risk not only for end-stage renal disease, but also for cardiovascular disease and death. Novel targets for better DN management urgently need to be identified, as ESRD can manifest despite strict glycaemic control and the application of various therapeutic approaches.

Early stage DN key pathological features include podocyte damage/loss and mesangial cell (MC) hypertrophy. The subsequent expansion of the myofibroblast progenitor population inside the kidney stroma and increased extracellular matrix (ECM) protein synthesis lead to glomerular basement membrane thickening and tubulo-interstitial fibrosis.

The renal structural alteration in DN is characterized by an early proliferation rate of both glomerular and tubular cells and a late accumulation of extracellular matrix proteins, as collagen IV and fibronectin leading to a progressive increase of the mesangial mass.

The role of miRs has been reported to contribute to fibrotic process in different pathological context including DN. miR21 has gained particular interest in mesangial cell expansion It has been recently reported that miR21 is also increased in urine from type 2 diabetic patients. Different miR21 targets have been reported to contribute to collagen production and fibrosis. PTEN up-regulation resulting in the activation of Akt-mTOR pathway seems to mainly contribute to this process. As a matter of fact, in the prior art it was shown that interfering with miR21 reverses kidney histological abnormalities in a preclinical model of DN. miR genes, like other genes, could be regulated by transcription factors. In this regard, miR-21 has been described as a STAT5 target gene in Jurkat cells as well as in mammary cells in response to prolactin. On the other hand, STAT5 itself could be controlled by different miRs, including miR222 and miR223 suggesting that the scenario is extremely complex.

Clinical and experimental nephrologists are working in differing fields to improve CDK outcomes. In particular, essential research, using in vivo and in vitro models, is currently looking to define the molecular basis for the principal pathways involved in CKD progression to ESRD and to find new therapeutic approaches to inhibiting renal fibrosis.

MSCs of different origin are currently the most widely studied stem cells in regenerative medicine. Although originally MSCs were thought to home in on and engraft injured tissues, where they differentiate and replace damaged cells, currently, the positive effects of MSC transplantation were demonstrated to result from their ability to release trophic mediators. Several studies have focused on extracellular RNA (exRNA) transporters, indicating that they may be present in biological fluids in form of vesicles including exosomes and microvesicles. As these vesicles have distinct biogenesis but share overlapping features and biological activities, the use of the inclusive term of "extracellular vesicles" (EVs) has been suggested. EVs have recently gained increased attention as well-preserved evolutionary cell-to-cell communication mechanisms. In particular, it has been found that stem cell-derived EVs may mimic the effect of the cells via the horizontal transfer of functional RNAs, miRs, lipids, and proteins when systemically or locally administrated in regenerative medicine. EVs recovered from different stem cell sources can share completely or partially their cargo. Moreover, enrichment of miRs or proteins can be detected depending of their origin.

Although general stem cell-derived EV functions have been the topic of recent studies in various pathological settings, how mechanistically they protect cells from damaging cues, as in response to high glucose, has been only partially investigated.

WO2011/143499 describes renal stem cells and the extracellular vesicles (EVs) thereof to be effective in the treatment of fibrosis.

WO2015/052526 describes the effect of microparticles (i.e. extracellular vesicles, EV) from neural stem cells for the treatment of fibrosis.

In order to look for a new therapeutic approach to fibrosis caused by hyperglycemia, the present inventors have analyzed the effects of EVs released from different stem cell sources on HG-induced collagen production (where "HG" stands for "high glucose"), paying particular attention on their effects on STAT5A miR21, miR222, miR100 and TGFβ expression. In particular, the treatment of diabetic nephropathy and renal fibrosis has been analyzed.

As it will be illustrated in detail in the experimental section of the present description, the results of their studies showed that EVs released from various types of stem cells protect mesangial cells from HG-induced collagen production. In particular, the inventors noticed that EVs, by transferring the microRNA designated as miR222, regulate the expression of STAT5 that in turn controls miR21, TGFb1 expression and matrix protein synthesis. Moreover, the inventors found that EVs, by driving changes in the balance between miR21 and miR100 in the recipient cell, could also indirectly contribute to the inhibition of collagen production. These results indicate that EVs released from various stem cells can transfer the relevant machinery to preserve mesangial cells from HG-mediated damage.

Therefore, a first aspect of the present invention is a pharmaceutically acceptable carrier carrying miR222, for use in the treatment of a fibrotic disease caused by hyperglycemia, in particular diabetic nephropathy and/or renal fibrosis. Treatment of other fibrotic diseases caused by hyperglycaemia, such as cardiomyopathy, nonalcoholic fatty liver (Ban and Twigg, 2009), in particular NASH (nonalcoholic steatohepatitis), and diabetic retinopathy is also envisioned.

BRIEF DESCRIPTION OF THE DRAWINGS

FIGS. 1A-1H are bar graphs reporting the results and analyses of short term high glucose stimulation inducing mesangial cell (MC) proliferation, collagen type IV production, and miR21 expression.

FIGS. 3A-3F are bar graphs reporting the results and analyses of regulating STAT5A expression in MCs subject to HG by MSCs and HLSCs-derived EVs.

FIGS. 4A-4F are bar graphs reporting the results and analyses of STAT5A expression regulation by extracellular vesicle miR.

FIGS. 9A and 9B graphically depict the results obtained expressed in terms of RQ (relative quantity), and FIGS. 9C and 9D graphically depict the results obtained expressed in terms of fold change, by applying methods of data analysis to calculate loading efficiency.

Figures 2A, 2B, 2C, 2D, 2E, 2F, 2G, 2H:
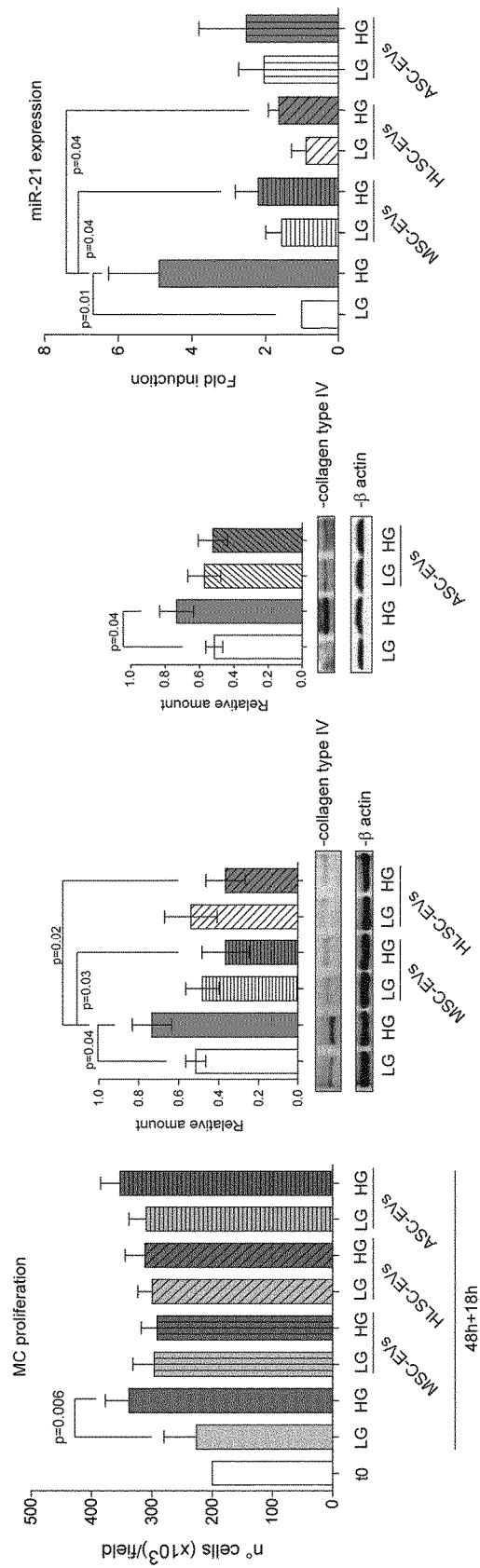
FIGS. 2A-2H are bar graphs reporting the results and analyses of the inhibition of collage production and miR21 expression in MCs by EVs from MSCs and HLSCs.

According to a preferred embodiment of the invention, the pharmaceutically acceptable carrier further comprises the microRNA "miR100".

miR222 and miR100 are microRNAs (miRNAs) known per se; their features and sequences may be found for example in the database designated as miRBase, under accession numbers MI0000299 and MI0000102, respectively.

The pharmaceutical effect can be attributed to the miRNAs contained in the pharmaceutical carrier. Any efficient transfection of the target cell with miRNAs is envisioned for effective use in the treatment of fibrotic diseases caused by hyperglycemia. An efficient transfection of miRNAs requires an appropriate pharmaceutical carrier, preferably in form of a micro- or nanoparticle. Such carriers are available commercially, including alginate-based (GEM, Global Cell Solutions), dextran-based (Cytodex, GE Healthcare), collagen-based (Cultispher, Percell), and polystyrene-based (SoloHill Engineering) microcarriers.

As an alternative, a pharmaceutical carrier for miRNAs may be a viral vector. Viral-based systems usually use retroviruses, lentiviruses, adenoviruses or adeno-associated viruses (AVV) as delivery vectors for, as disclosed for example in Ningning Yang. An overview of viral and nonviral delivery systems for microRNA. Int J Pharm Investig. 2015 October-December; 5(4): 179-181. Therefore, the selection and use of a suitable carrier for the miRNA is well within the capabilities of the person skilled in the art.

An even more preferred pharmaceutical carrier for miRNAs is a vesicle, such as a liposome or an extracellular vesicle (EV). Extracellular vesicles, such as cell derived microvesicles or exosomes are the most preferred pharmaceutical carriers.

Therefore, according to another preferred embodiment of the invention, the pharmaceutically acceptable carrier is an extracellular vesicle (EV) derived from a stem cell, preferably from an adult stem cell, more preferably from a mesenchymal stem cell (MSC), such as e.g. a bone marrow stromal stem cell, or an adipose stem cell (ASC), or a non-oval human liver progenitor cell (HLSC). HLSC a method of obtaining thereof, are disclosed in International patent application published as WO2006126219.

A further aspect of the invention is a composition of extracellular vesicles isolated from the conditioned medium of a stem cell, preferably from the conditioned medium of an adult stem cell, more preferably from the conditioned medium of a mesenchymal stem cell (MSC) or a human liver stem cell (HLSC), for use in the treatment of a fibrotic disease caused by hyperglycaemia, preferably diabetic nephropathy, renal fibrosis, cardiomyopathy or nonalcoholic fatty liver in particular NASH, or diabetic retinopathy. The extracellular vesicles of the claimed composition preferably contain the microRNA miR222 and optionally the microRNA miRNA100.

The extracellular vesicle (EV) for use according the invention is a naturally occurring EV or, alternatively, an EV which has been engineered to contain a significantly higher amount of miR222 or miR100 compared to the naturally-occurring extracellular vesicle (EV), and which is obtainable by loading miR222 or miR100 to an isolated extracellular vesicle ex vivo.

European patent application published as EP 2010663 provides the person skilled in the art with instructions on how to engineer EVs with specific miRNAs. Techniques known to the skilled person introducing RNA into vesicles or exosomes are transfection or co-incubation. Known transfection methods are for example electroporation, lipofection, microinjection, transfection by viral and nonviral vectors, magnet assisted transfection and sonoporation. Consequently, an engineered EV to which miR222 or miR100 has been introduced ex vivo is another aspect of the invention.

As illustrated in further detail in the experimental part that follows, a suitable method to assess the significantly higher amount of miR222 or miR100 compared to the naturally-occurring extracellular vesicle (EV) is the ΔΔCT method of qPCR data analysis.

Expressed as a relative value, the loading efficiency, i.e. the amount of the target molecule (i.e. either miR222 or miR100) which is present in the engineered EV of the invention as compared to the natural amount is of at least 2-fold. Alternatively, the loading efficiency may be expressed in absolute terms as the number of loaded target molecules per EV. It is envisaged that this value may range from about $1 \times 10^3$ to about $1 \times 10^5$ target molecules/EV higher that the natural amount.

The following experimental part, which discloses the experiments carried out by the inventors with EVs derived from MSCs and HLSCs, is provided by way of illustration only and is not intended to limit the scope of the invention as determined by the appended claims.

The results obtained by the inventors demonstrated that, in mesangial cells, HG drives the expression of TGFβ and the production of collagen via STAT5A-mediated pathway. By expressing a ANSTAT5 construct in mesangial cells cultured in HG, the inventors demonstrated that STAT5A activation controls miR21 expression. The inventors have also shown that EVs released from MSCs and HLSCs protect mesangial cells from HG-induced collagen production. In particular, they have noticed that EVs, by transferring miR222 to mesangial cells, regulate the expression of STAT5A that in turn controls miR21 content, TGFβ expression and matrix protein synthesis. These results were further confirmed by over-expressing miR222 in mesangial cells cultured in HG conditions. Moreover, by over-expressing miR100, the inventors demonstrated that changes in the balance between miR21 and miR100 in the recipient cell, resulting from transfer of EV cargo, lead to mTOR down regulation and impairment of both TGFβ expression and collagen production. Interestingly, these effects were only detected in HG-cultured cells.

EXAMPLE 1

Materials and Methods

Cell Cultures

Human mesangial cells (MCs) were cultured in DMEM with 1.0 g/l D-glucose (low glucose, LG) or DMEM 25 mM D-glucose (high glucose, HG). MCs were also cultured in DMEM LG and HG without fetal bovine serum (FBS) for 24 hours in the presence of MSC- or HLSC-derived EVs. The same number of EVs was used to stimulate MC in all experimental conditions (7000 EV/target cell).

Isolation and quantification of MSC- and HLSC derived-EVs MSCs and HLSCs were cultured in EndoGRO Medium, without fetal bovine serum, for 24 h in order to collect EVs from supernatants. After being centrifuged at 3000 g for 30 min to remove debris, cell-free supernatants were submitted to differential ultracentrifugation at 10 000 and 100 000 g (Beckman Coulter Optima L-90K ultracentrifuge; Beckman Coulter, Fullerton, Calif. USA) for 3 h at 4° C. EVs were either used fresh or were stored at −80° C. after re-suspension in DMEM which was supplied with 1% DMSO (Deregibus 2007). Frozen EVs were washed and pelleted by 100k g ultracentrifugation to remove DMSO before cellular experiments. No difference in biological activity was observed between fresh and stored EVs. The protein content of EVs was quantified using the Bradford method (Bio-Rad, Hercules, Calif., USA). Any possible contamination was tested using a Limulus amebocyte assay (concentration <0.1 ng/ml) (Charles River Laboratories, Inc., Wilmington, Mass., USA). EV size distribution analysis was performed using a NanoSight LM10 (NanoSight Ltd, Minton Park UK). The particles in the samples were illuminated using a laser light source and the scattered light was captured by camera and analyzed using Nanoparticle Tracking Analysis (NTA). NTA automatically tracked and sized particles according to Brownian motion and the diffusion coefficient (Dt).

Cell Proliferation

Cell proliferation in both LG and HG conditions with or without EVs was assayed by direct cell count by three different operators.

Western Blot Analysis

MCs were lysed and protein concentrations obtained as previously described (Olgasi, 2014). 50 μg proteins were subjected to SDS-PAGE, transferred into nitrocellulose membranes and processed as previously described (Olgasi, 2014). Densitometric analysis was used to calculate the differences in the fold induction of protein levels which were normalized to actin. Values are reported as relative amounts.

RNA Isolation and Quantitative Real-Time PCR (qRT-PCR)

Total RNA was isolated from MCs using the TRIzol reagent (Invitrogen) according to manufacturer's instructions. RNA was quantified spectrophotometrically (Nanodrop ND-1000, Wilmington, Del., USA). RNA from cells was then reverse-transcribed using a TaqMan microRNA RT kit specific for miR-222, or Syber Green microRNA RT Kit specific for miR-21 and miR-100. Thus RNA was subjected to qRT-PCR using a TaqMan/Syber microRNA assay kit and the ABI PRISM 7700 sequence detection system (Applied Biosystems, Foster City, Calif., USA). MiR expression was normalized to the small nuclear RNA, RNU6B.

Transfection of MCs with PremiR-100, and PremiR-222

Gain-of-function experiments were performed in mesangial cells transfected either with the pre-miR negative control or the pre-miR100 and premiR-222 precursor (Applied Biosystem), according to manufacturer's instructions. All proteins extracted from cellular lysis of these samples were then subjected to western blot and all RNAs were analysed with RT-PCR.

Transfer of miRs from EVs to MCs

In order to analyze miR-222 transfer from EVs to MCs, miR transfer experiments were conducted as previously described by Yuan (Yuan, 2009). $5 \times 10^5$ cells/well of MCs were incubated with the a transcriptional inhibitor, α-amanitin, (Lee, 2004) in the absence or in the presence of EVs pretreated or not with RNAse. Total RNA from MCs, treated as above, were subjected to qRT-PCR for miR expression. As an indirect measure of miR transfer, the inventors determined the difference in Ct values between α-amanitin treated cells in the absence or in the presence of EVs pretreated or not with RNAse; a positive value indicated transfer of miR into target cells. If no signal was detected, a Ct value of 40 was assigned to the sample.

Transfection of Dominant Negative (ΔN) STAT5A Construct.

In selected experiments, MCs cultured for 48 hours in the presence or absence of HG were transiently transfected with the ANSTAT5 construct (Defilippi, 2005, Zeoli, 2008). Then cells were processed to obtain cell extracts for Western blot analysis or total RNA isolation to evaluate miR21 expression.

Senescence Assay

Senescence assay Senescence was evaluated by measuring the acidic β-galactosidase activity of N-ASCs that were differently cultured, as previously described (Togliatto, 2010).

Statistical Analysis

All data are presented as mean or percentage±s.e.m. The D'Agostino-Pearson test was used to test normality. Data on biometric measurements of patients and controls, on the in vitro angiogenic, migration, adhesion and senescence assays, on miR expression, cell proliferation, loss- and gain-of-function experiments and finally on densitometric analysis for western blots were analyzed using Student's t-tests for two-group comparison and using one-way analysis of variance, followed by Tukey's multiple comparison test, for 3 groups. Three experiments performed in triplicate were the minimum sample size ensuring 90% statistical power between experimental groups, with a probability level of 0.05, two-tailed hypothesis. The cutoff for statistical significance was set at $P<0.05$ (*$P<0.05$, $P<0.01$, *$P<0.001$). All statistical analyses were carried out using GraphPad Prism version 5.04 (GraphPad Software, Inc., La Jolla, Calif., USA).

Results

Short Term High Glucose Stimulation Induces Mesangial Cell (MC) Proliferation, Collagen Type IV Production and miR21 expression.

To mimic acute hyperglycaemia-mediated mesangial cell damage MCs were cultured in high glucose medium (25 mM) for 48 hours. Proliferation and senescence were analyzed. As shown in FIG. 1A HG promotes a significant increase in MC proliferation as shown by the number of cells and by cyclin D1 content (FIG. 1B). No changes in the number of senescent MCs were detected (FIG. 1C). MC collagen production is a hallmark of glomerular damage. Thus, collagen production was evaluated in MCs challenged with HG. Western blot analysis on both cell total lysates and supernatants showed a significant increase in collagen type IV production when compared with low glucose treaded cells (FIGS. 1D and E). The increase in collagen production indicates MC shift to a fibrotic secretive phenotype. TGFβ already barely produced by MC was further increased by HG treatment (FIG. 1F). miR 21, a well known miRNA involved in diabetic nephropathy, is known to induce mesangial cell matrix expansion. Consistently HG treatment was found to induce miR21 expression (FIG. 1G). The involvement of this signaling pathway was investigated. The inventors found that, even in MC treated with HG, high level of mTOR could be detected (FIG. 1H).

EVs from MSCs and HLSCs Inhibit Collagen Production and miR21 Expression in MCs

EVs were recovered from MSCs, and HLSCs and assayed on MC proliferation and collagen production. Thus, MCs cultured in LG or HG concentration for 48 hours were serum starved and subjected to EVs treatment for 18 hours. As shown in FIG. 2A, EVs did not interfere with MC proliferation. However, when collagen production was evaluated, EVs recovered from MSCs and HLSCs significantly reduced collagen production (FIGS. 2B and C). Consistently, down-regulation of miR21 (FIG. 2D), mTOR (FIG. 2E-F) and TGFβ expression were detected (FIG. 2G-H).

MSCs and HLSCs-Derived EVs Regulate STAT5A Expression in MCs Subjected to HG

The observation that EVs derived from MSCs and HLSCs affect miR21 expression led the inventors to investigate whether STAT5A could be involved in its regulation. To this end MCs treated with HG in the presence or in the absence of EVs were analyzed for STAT5A activation. As shown in FIG. 3A, STAT5A underwent activation in response to HG treatment, effect which was inhibited by EV treatment (FIG. 3B-C). The observation that a reduced STAT5A expression was detected in these experimental conditions strongly suggests the possibility that EV cargo might regulate its expression. To investigate this possibility a ANSTAT5A construct was transfected in MCs (FIG. 3D) and miR21 expression analyzed. As reported in FIG. 3E, inhibition of STAT5A activation led to down-regulation of miR21 in HG-treated MCs. Consistently, when collagen production was analyzed in these experimental conditions, its expression was found almost completely suppressed. Interestingly, it was also demonstrated that inhibition of STAT5A signaling pathway prevents HG-mediated TGFβ expression as well (FIG. 3F).

EV miR Cargo Regulates STAT5A Expression

MSC and HLSC EV mirnomic has been previously reported (Collino 2010). The inventors investigated whether miRs expressed in EVs from such cellular sources can be relevant in regulating the signaling pathway activated by HG. Among them miR222 is included. miR222 has been reported to be a direct post-transcriptional regulator of STAT5A. Therefore, the expression of miR222 was evaluated in HG-cultured MCs treated with EV. As shown in FIG. 4A, miR222 is down regulated upon HG treatment while increased upon EV treatment. That this effect depended on the release of EV-miR222 content into MCs was demonstrated by experiments performed in the presence of amanitin and EVs pretreated or not with RNAse (FIG. 4B). To further confirm these results gain-of function experiments were performed using MCs transfected with premiR222 and cultured in HG conditions. As expected over-expression of miR222 led to a drastic reduction of STAT5A content as well as miR21 cellular content, TGFβ expression and collagen production in HG treated MCs (FIG. 4D-F). More importantly, such event did not occur in LG-cultured MCs, indicating that a specific signaling pathway is induced by the hyperglycaemic milieu.

Figure 5A:
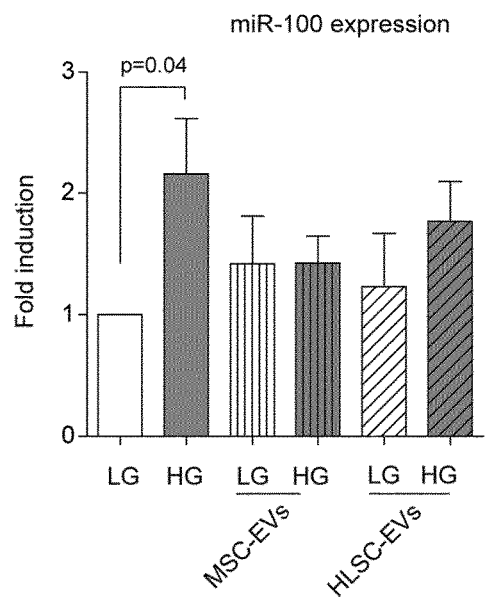
FIGS. 5A-5C are bar graphs reporting the results and analyses of promoting miR100 post- transcriptional activity by EV-mediated miR21 down-regulation.
Figure 5B:
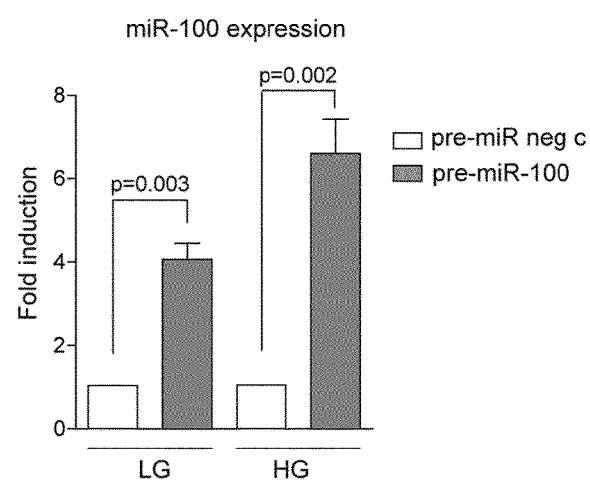
Figure 5C:
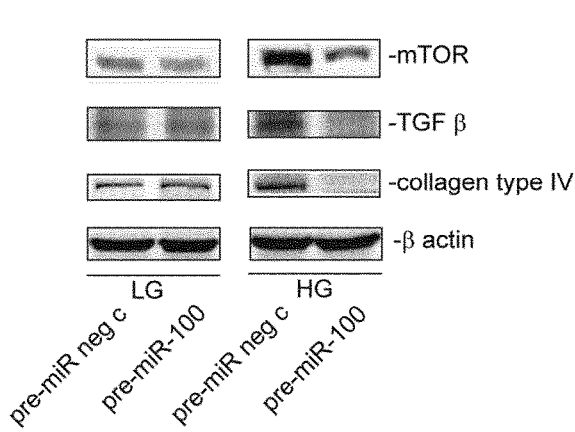
Figure 5D:
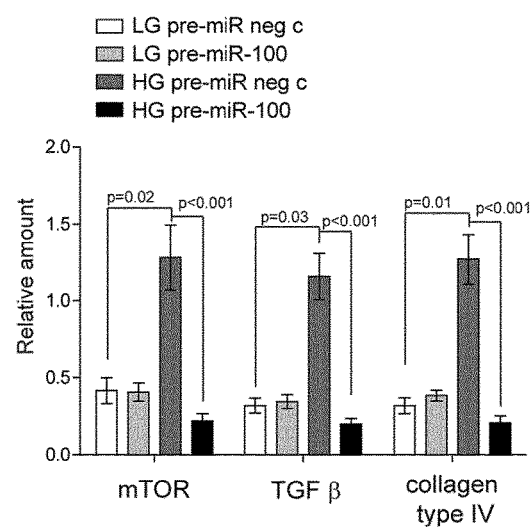

EV-Mediated miR21 Down-Regulation can Promote miR100 Post-Transcriptial Activity Which Contributes to Inhibition of Collagen Production The inventors investigated whether miR100 can also contribute to EV-mediated effects. First, miR100 expression was evaluated in MCs subjected to EV treatment. As shown in FIG. 5A, while miR100 MC content increased upon HG treatment, no changes in its content could be detected after EV treatment. However, as the balance of intracellular miRs could direct specific biological responses, the inventors hypothesized that the decreased miR21 intracellular content associated with EV treatment could good deed miR100 post-transcriptional activity. To validate this hypothesis gain-of function experiments using premiR100 were performed in HG-treated MCs. Indeed, data reported in FIG. 5B demonstrate that when miR100 expression is favoured with respect to miR21 it can drive signals, mediated by mTOR down-regulation, which result in inhibition of MC TGFβ expression and collagen production (FIG. 5C-D). Again, miR100 over-expression did not impact on LG-cultured MCs (FIG. 5C-D). Collectively these data indicate that the fine tuning of miR content into recipient cells, associated with EV treatment, might also contribute to their healing properties.

EXAMPLE 2

In Vivo Model of Diabetic Nephropathy: Treatment with EVs-Derived Stem Cells (SC-EVs)

Figure 7A:
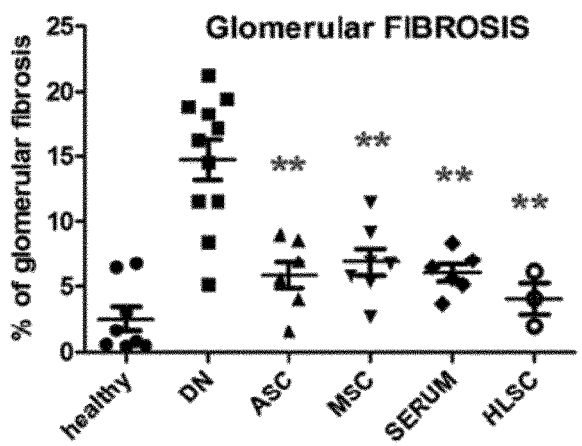
Figure 7B:
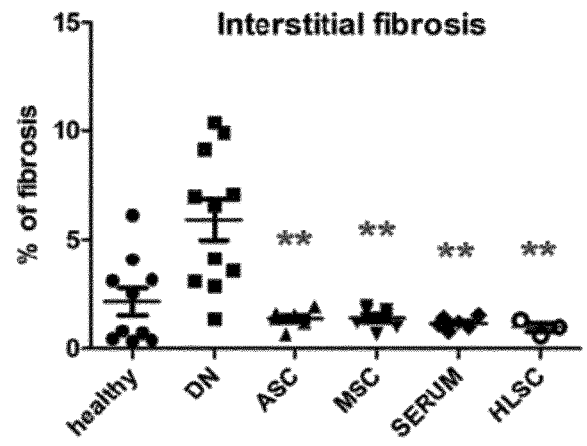
Figure 8:
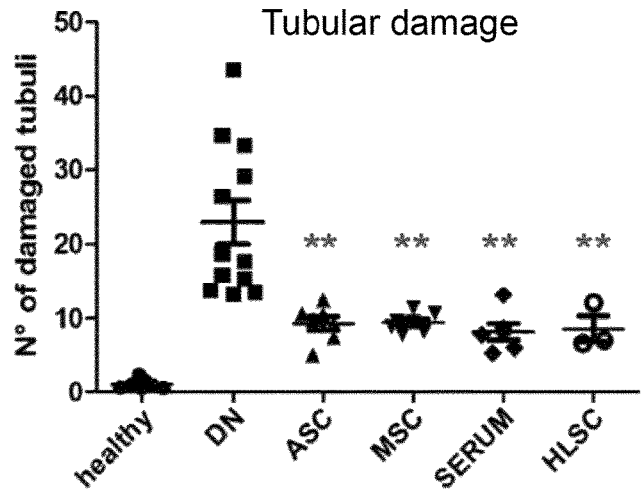

An experimental study was conducted in order to investigate whether EVs released from different stem cell sources or serum may interfere with damage in an experimental diabetic nephropathy. To this end, mice were subjected to streptozotocin (STZ) treatment (35 mg/kg for 4 consecutive days, i.p.) to produce an animal model of hyperglycaemia. After the onset of diabetes at time zero (T0), the diabetic mice were subjected to 5 EV-treatments ($1 \times 10^{10}$ each) once a week (T7, T14, T21 and T28). The following parameters were measured after 1 month from the onset of diabetes (T30, end point): glycaemia, weight, urinary albumin/creatinine ratio, urinary pH, plasma creatinine (CREA). Additionally, the kidneys were subjected to the following histological analyses: glomerular and interstitial fibrosis, glomerular area, Bowman's space, tubular damage. The results obtained are illustrated in FIG. 6-8, which show the results obtained for each of the following mice groups: 10 healthy mice; 15 diabetic mice (DN); 10 MSC-EVs-treated mice; 10 Serum EVs-treated mice; 10 ASC-EVs-treated mice and 6 HLSC-EVs-treated mice.

Figure 6:
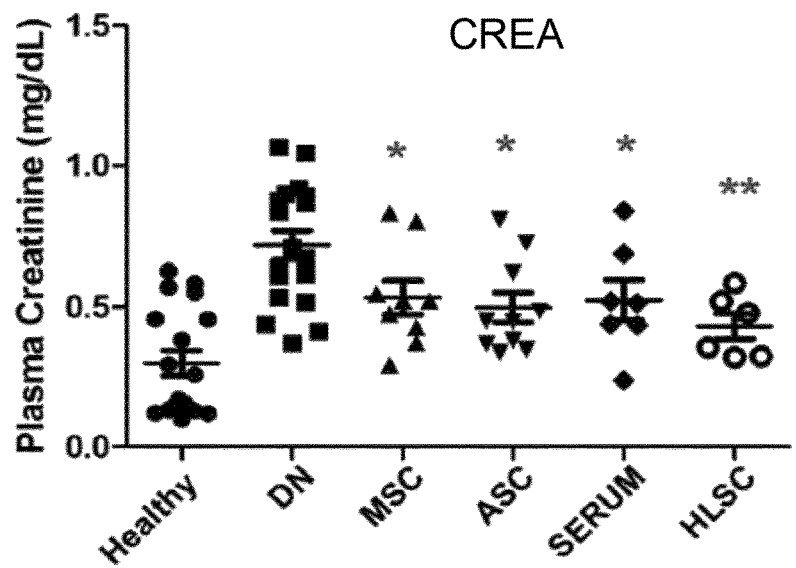
FIG. 6, FIGS. 7A and 7B, and FIG. 8 graphically depict the results obtained in a study to investigate whether extracellular vesicles released from different stem cell sources of serum can interfere with damage in an experimental diabetic nephropathy.

FIG. 6 shows that plasma creatinine was increased in diabetic mice and that a significant reduction in plasma creatinine occurred in mice treated with all EV sources. FIG. 7 shows that a significant improvement in terms of reduction of collagen deposition within glomeruli and in the interstitial space occurred in diabetic mice treated with EVs. FIG. 8 shows that treatment with all EVs tested led to a relevant improvement of tubular damage as compared to diabetic mice. All data are expressed as mean±SEM. *$p<0.05$, versus DN, **$p<0.001$ versus DN. Furthermore for all EV sources a significant reduction in ACR and a significant restoration of pH values was shown.

EXAMPLE 3

Extracellular Vesicles Enrichment with miRNA by Transfection of Stem Cells: Method for EV Engineering In order to enrich miRNA content in stem cell derived EVs, mesenchymal stem cells (MSCs) were transfected by electroporation using the Neon transfection system (Invitrogen) according to the manufacturer's instructions. 600 pmol of a mimic which is not present in naturally-occurring MSCs, i.e. cel-miR-39, were used to enrich $1 \times 10^6$ MSCs that were seeded in complete medium supplemented with foetal calf serum (FCS) and without antibiotics. A scramble mimic was used as the negative control (SCR).

The following day the medium was replaced and the transfected cells were incubated overnight with RPMI without FCS. The supernatant was collected and centrifuged at 2,000 g for 15 minutes to remove cell debris and apoptotic bodies and then concentrated at 4° C. using ultrafiltration units (Amicon Ultra-PL 3, Millipore) with a 3 kDa molecular weight cut-off. A Concentrated Medium (CM) containing EVs was supplemented with 1% dimethyl sulfoxide and kept at −80° C. until use.

The RNA analysis was carried out by precipitation of the Concentrated Medium containing EVs using PEG at 4° C. overnight. The EV pellet was washed twice with PBS 1× and the RNA was extracted using the RNA/DNA/Protein Purification Plus Kit (Norgen Biotek). RNA samples were retrotranscribed and quantitative real time PCR was performed with the miScript PCR system (Qiagen). RNU6B or RNU48 were used as the housekeeping controls (CTL). EVs from MSCs subjected to electroporation with no target (cel-miR-39) and no scramble were also used as a further control (EP).

FIG. 9 shows the results obtained, expressed in terms of RQ (relative quantity) and fold change, obtained by applying the comparative or $\Delta\Delta C^T$ method of qPCR data analysis to calculate the loading efficiency.

In the comparative or $\Delta\Delta C^T$ method of qPCR data analysis, the $C^T$ values obtained from two different experimental RNA samples are directly normalized to a housekeeping gene and then compared. First, the difference between the $C^T$ values ($\Delta C^T$) of the gene of interest and the housekeeping gene is calculated for each experimental sample. Then, the difference in the $\Delta C^T$ values between the experimental and control samples $\Delta\Delta C^T$ (i.e. calibrators) is calculated.

The fold-change in expression of the gene of interest between the two samples is then $$RQ = 2^{-\Delta\Delta Ct}$$

In the experiment at issue RQ was calculated as follows:

$$\Delta C^T = C^{T\ target} - C^{T\ reference}\ (C^T = \text{cycle threshold})$$

where the target is cel-miR-39 and the reference is the housekeeping control (RNU6B or RNU48).

$\Delta\Delta C^T = \Delta C^T$ test sample − $\Delta C^T$ calibrator sample, where the calibrator sample are EVs derived from untreated cells and the test sample are the EVs derived from treated cells.

FIG. 9 shows that MSCs can be effectively loaded with miRNA molecules by electroporation and that the target miRNA molecules are present both in the MSCs themselves and in the EVs derived from the loaded MSCs. The amount of target miRNA loaded to the EVs is approximately 100-fold lower than the amount of target miRNA loaded to the MSCs.

Therefore, a reasonable estimate of the loading efficiency expressed as the number of loaded target molecules/EV is comprised within the range of from $1 \times 10^3$ to $1 \times 10^5$.

The upper limit of this range is based on FIG. 5a of Fuhrmann et al. (2014), which shows a loading efficiency approximately ranging from $10^4$ and $10^5$, and on the NTA count of the EV particles obtained upon transfection of MSCs with various types of miRNAs,

REFERENCES

C R Ban and S M Twigg., Fibrosis in diabetes complications: pathogenic mechanisms and circulating and urinary markers. Vasc Health Risk Manag. 2008; 4(3):575-96.

Ningning Yang. An overview of viral and nonviral delivery systems for microRNA. Int J Pharm Investig. 2015 October-December; 5(4): 179-181.

Deregibus M C, Cantaluppi V, Calogero R, Lo Iacono M, Tetta C, Biancone L, Bruno S, Bussolati B, Camussi G., Endothelial progenitor cell derived microvesicles activate an angiogenic program in endothelial cells by a horizontal transfer of mRNA (2007), Blood, 110(7):2440-8.

Olgasi, C., et al. DNA vaccination against membrane-bound Kit ligand: a new approach to inhibiting tumour growth and angiogenesis. Eur J Cancer. 50, 234-246 (2014).

Yuan, A., et al. Transfer of microRNAs by embryonic stem cell microvesicles. PLoS One. 4, e4722 (2009).

Lee, Y., et al. MicroRNA genes are transcribed by RNA polymerase II. EMBO J. 23, 4051-4060 (2004).

Togliatto G, Trombetta A, Dentelli P et al. Unacylated ghrelin rescues endothelial progenitor cell function in individuals with type 2 diabetes. Diabetes. 59, 1016-1025 (2010).

Collino F, Deregibus M C, Bruno S, Sterpone L, Aghemo G, Viltono L, Tetta C, Camussi G., Microvesicles derived from adult human bone marrow and tissue specific mesenchymal stem cells shuttle selected pattern of miRNAs (2010), PLoS One. 2010 Jul. 27; 5(7):e11803.

Fuhrmann G. et all Control Release. 2015 May 10; 205:35-44. doi: 10.1016/j.jconrel.2014.11.029. Epub 2014 Dec. 4.

The invention claimed is:

1. An extracellular vesicle (EV) engineered to contain miR222 or miR100 in an amount between $1 \times 10^3$ and $\times 10^5$ molecules/EV higher than the amount present in the naturally-occurring extracellular vesicle (EV), which is obtainable by loading miR222 or miR100 to an isolated extracellular vesicle ex vivo.

2. The engineered extracellular vesicle (EV) according to claim 1, wherein the extracellular vesicle has been isolated from a stem cell or body fluid.

3. The engineered extracellular vesicle (EV) according to claim 2, wherein the stem cell is an adult stem cell.

4. The engineered extracellular vesicle (EV) according to claim 1, wherein the miR222 or miR100 is loaded to the EV by a transfection method selected from the group consisting of electroporation, lipofection, microinjection, transfection by viral and nonviral vectors, magnet assisted transfection, co-incubation, and sonoporation.

* * * * *